(12) United States Patent
Allgeier et al.

(10) Patent No.: US 7,060,819 B2
(45) Date of Patent: Jun. 13, 2006

(54) PROCESS FOR PRODUCING HEXAMETHYLENEDIAMINE AND AMINOCAPRONITRILE FROM ADIPONITRILE, WHEREIN THE HEXAMETHYLENEDIAMINE CONTAINS LESS THAN 100 PPM TETRAHYDROAZEPINE

(75) Inventors: Alan Martin Allgeier, Wilmington, DE (US); John J. Ostermaier, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 436 days.

(21) Appl. No.: 10/663,479

(22) Filed: Sep. 15, 2003

(65) Prior Publication Data

US 2005/0059822 A1    Mar. 17, 2005

(51) Int. Cl.
*C07D 201/16*    (2006.01)
*C07D 223/02*    (2006.01)

(52) U.S. Cl. ...................................... 540/484; 540/540
(58) Field of Classification Search ................ 540/484, 540/540

See application file for complete search history.

(56) References Cited

U.S. PATENT DOCUMENTS

| 6,153,748 | A  | 11/2000 | Fuchs et al. |
|---|---|---|---|
| 6,169,199 | B1 | 1/2001 | Rehfinger et al. |
| 6,252,115 | B1 | 6/2001 | Luyken et al. |
| 6,300,497 | B1 | 10/2001 | Rehfinger et al. |
| 6,348,630 | B1 | 2/2002 | Merk et al. |
| 2003/0023083 | A1 | 1/2003 | Luyken et al. |

FOREIGN PATENT DOCUMENTS

WO    2005/000785    1/2005

*Primary Examiner*—Taofiq Solola

(57) ABSTRACT

Process for making both ACN and HMD from partial hydrogenation of ADN by using a combination of distillations resulting in the formation of a mixture of HMD and THA that can be hydrogenated to produce a mixture of HMD and HMI that can be separated easily by simple distillation.

2 Claims, 1 Drawing Sheet

PROCESS FOR PRODUCING HEXAMETHYLENEDIAMINE AND AMINOCAPRONITRILE FROM ADIPONITRILE, WHEREIN THE HEXAMETHYLENEDIAMINE CONTAINS LESS THAN 100 PPM TETRAHYDROAZEPINE

BACKGROUND

When one carries out the hydrogenation of adiponitrile (ADN) to produce the fully hydrogenated product, hexamtheylenediamine (HMD), or the partially hydrogenated product, epsilon-aminocapronitrile (ACN), one inevitably produces some byproducts, including certain imines. Imines are problematic in further processing the HMD and ACN to Nylon 6,6 and Nylon 6, respectively, because the imines impart an undesirable color to the nylons, and the imines may limit the molecular weight that the nylon polymers can attain. (Generally, high molecular weights are preferred for nylon.) The most common problematic imine in ADN hydrogenation is tetrahydroazepine (THA). One can use a gas chromatograph to measure THA, or a polarograph to measure all of the so-called polarographically reducible impurities (PRI) in the measured sample, the major component of the PRI being THA. The polarographic measurement generally will be somewhat higher than the chromatographic measurement, because a polarograph measures polarographically reducible impurities other than THA.

Conceptually, one may envisage the making of HMD by allowing ADN molecules to move slowly through a hydrogenation reactor with a low space velocity, providing plenty of time for hydrogen to react with ADN to convert both of the ADN nitrile groups to amine groups. In contrast, if ADN is allowed to move quickly through the hydrogenation reactor at a higher space velocity, thereby shortening the time that the hydrogen can react with the ADN, the crude reaction product will contain the fully hydrogenated product, HMD, the partially hydrogenated product, ACN, as well as unreacted ADN. Operating in this latter way, generally referred to as "partial hydrogenation," would allow one hydrogenation reactor to be used to prepare intermediates for two types of nylons: ACN for Nylon 6 and HMD for Nylon 6,6. It is known that when one does partial hydrogenation, the PRI (mainly THA) levels will be higher than if one does complete hydrogenation. With the increased reaction time inherent in complete hydrogenation, the THA can react with the hydrogen to convert the carbon-nitrogen double bond of the THA into a carbon-nitrogen single bond, leading to the formation of a product called hexamethyleneimine (HMI), perhaps confusingly named, because its molecular structure does not meet one definition of an imine, namely the presence of a carbon-nitrogen double bond.

A necessary part of a partial hydrogenation process is the removal of PRI (mainly THA) from the crude ADN hydrogenation product before polymerization. Different approaches for accomplishing this have been disclosed in the art, including various distillations that can separately recover unreacted ADN, ACN and HMD. These distillations, however, tend to leave the PRI (mainly THA) in the ACN fraction that results from the distillation. Some investigators have proposed hydrogenating the PRI in the ACN fraction (see U.S. Pat. No. 6,1537,48), but this approach creates the potential of further hydrogenating the ACN to HMD, thus reducing the yield of the desirable ACN, and necessitating further distillations to separate the ACN from the HMD. Others have suggested separation by electrochemical reduction.

A commercially viable partial hydrogenation process must be capable of producing HMD that contains low levels of THA, generally less than 200 ppm, preferably less than 100 ppm.

SUMMARY OF THE INVENTION

Accordingly, the present invention can be defined as a process for co-producing HMD and ACN from ADN, wherein the HMD contains less than 200 ppm THA, said process comprising the steps of:

(1) contacting ADN and hydrogen in the presence of a hydrogenation catalyst to produce a reaction product that comprises HMD, ACN, THA, and unreacted ADN;

(2) distilling the reaction product to provide a distillate that comprises HMD and THA;

(3) contacting the distillate with hydrogen in the presence of a hydrogenation catalyst, thereby providing a hydrogenation product that comprises HMD and HMI, said hydrogenation product containing less than 200 ppm THA; and (4) distilling the hydrogenation product to provide a final distillate that comprises HMI and a bottoms that comprises HMD that contains less than 200 ppm THA and is substantially free of HMI.

BRIEF DESCRIPTION OF THE DRAWING

The Drawing consists of one FIGURE showing a block diagram illustrating the process of the invention.

DETAILED DESCRIPTION OF THE INVENTION

Figure 1:
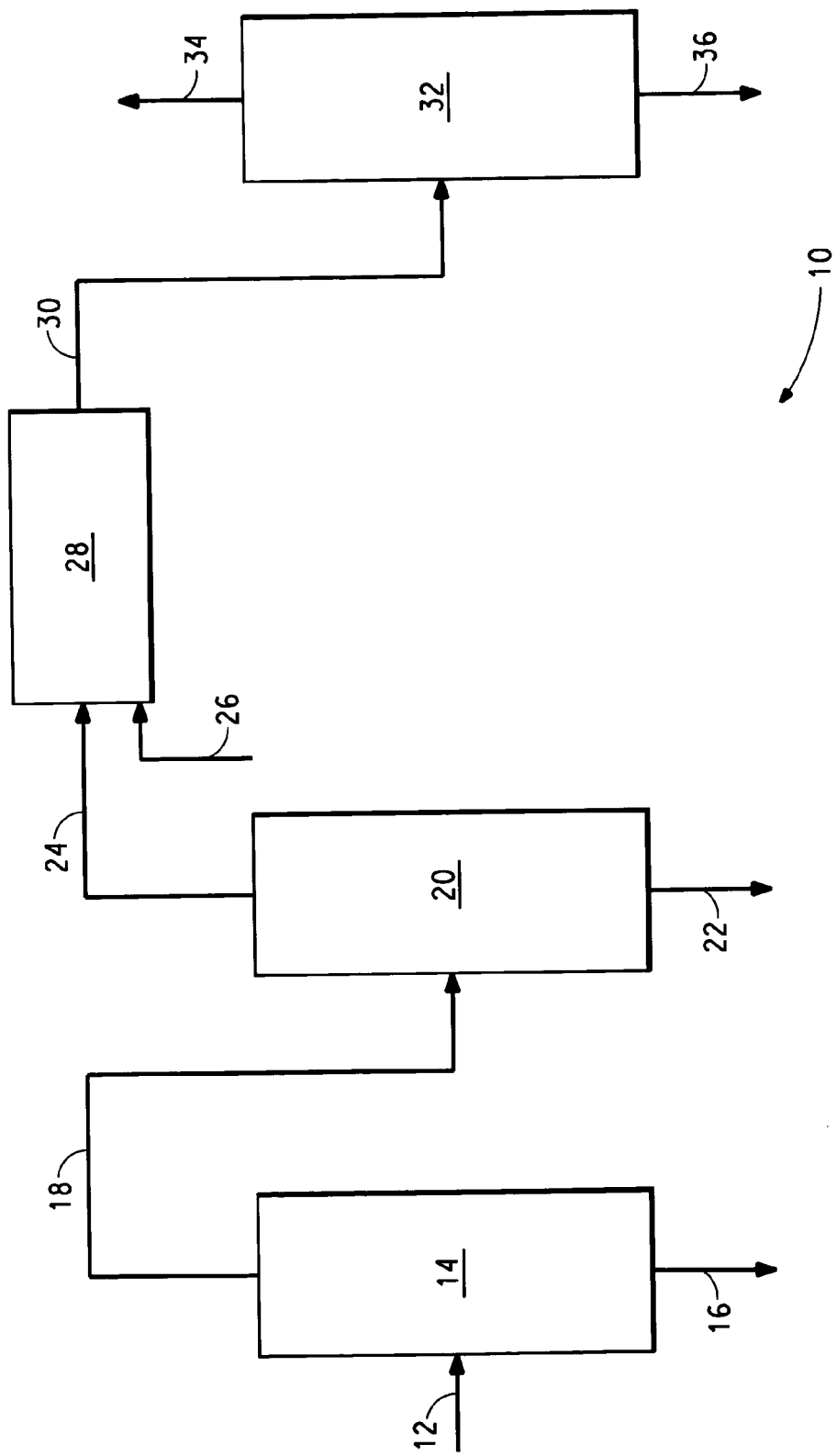

Referring now to FIG. 1, there is shown in schematic form apparatus 10 for carrying out an embodiment of the present invention. A stream 12 comprising ADN, ACN, HMD, and THA that is the product of a partial hydrogenation of ADN is introduced into a distillation column 14 having a head pressure less than about 100 torr (13.3 kPa). The column preferably contains structured packing.

The partial hydrogenation may be carried out in the presence of an ammonia solvent. If such a solvent is used, the solvent should be removed from the partial hydrogenation product prior to introducing such product into the distillation column 14. The removal of ammonia solvent may be accomplished using a stripper (not shown), in which case the ammonia will be removed as an overhead and the bottoms will be fed to the distillation column 14.

Distillation column 14 produces a bottoms 16 that comprises ADN, and a distillate that comprises ACN, HMD, and THA.

The distillate 18 is introduced into a second distillation column 20 having a head pressure less than about 400 torr (53.2 kPa), preferably less than about 300 torr (39.9 kPa), most preferably less than about 200 torr (26.6 kPa). The column preferably contains structured packing. The distillation column 20 produces a bottoms 22 that comprises ACN and a distillate 24 that comprises THA and HMD.

The distillate 24 is introduced, together with hydrogen 26 into a hydrogenation reactor 28 in which a hydrogenation catalyst (not shown) is present. The THA and hydrogen will react in the reactor 28 to convert the THA into HMI.

The reaction product 30 of the reactor 28 is introduced into a third distillation column 32 with atmospheric head pressure to produce a distillate 34 that comprises HMI and a bottoms 36 that comprises HMD.

The hydrogenation catalyst can be based on elements of the transition metal groups of the periodic table, such as Ni, Co, Rh, Pd, and Pt. Iron catalysts should work as well. Ruthenium, however, did not work very well. Preferred catalysts are Raney Nickel and Raney Cobalt. Promoter elements added to the catalyst may improve performance. Examples of suitable promoters are lithium, sodium, potassium, magnesium, calcium, titanium, molybdenum, chromium, iron, palladium, platinum, copper, aluminum, and silicon. There are a variety of ways known in the art for preparing the catalysts, and many catalysts are commercially available. The catalysts could be on a support material such as carbon, alumina or silica, or they could be provided without a support material, for example in the form of so-called Raney-type catalysts or reduced metal oxides which are nominally all metallic in content.

The hydrogenation reaction may be carried out at different temperatures from 50 to 180 degrees C. The choice of temperature is dependent upon the catalyst. Very good results were obtained at 80 to 90 degrees C. with Raney-type nickel catalysts. The hydrogenation reaction may be carried out at different pressures from 250 psig (1.825 MPa) to 5000 psig (34.5 MPa), although economics favor the use of lower pressures such as 400 to 1000 psig (2.86 MPa to 7.0 MPa). The reaction may be carried out without a solvent. Various reactor configurations are possible, and include a batch stirred tank reactor and a packed bed reactor.

EXAMPLE

The following example differs from the embodiment of the invention shown in the Drawing, in that two distillation columns were not used to produce the mixture of HMD and THA that was subjected to hydrogenation to produce a mixture of the HMD and HMI with a low THA content. Rather, in this example, which may be regarded as representing an alternative embodiment of the invention, a single distillation column was used (after an ammonia stripping column) to produce a distillate that contained the mixture of HMD and THA, and a side draw was removed that contained primarily an ACN-rich mixture of ACN and HMD. The ACN and HMD in this latter mixture can be separated by simple distillation to recover a substantially pure ACN material.

ADN was partially hydrogenated in the presence of a hydrogenation catalyst to produce a reaction product containing 1000 ppm THA, 39.3% HMD, 24.2% ACN and 24.4% unreacted ADN. The reaction product was fed to a stripper column to remove dissolved ammonia. The stripper column contained 10 feet of Koch/Glitch BX packing directly above a reboiler and 25 Oldershaw trays above the BX packing. There was a condenser at the top of the column above the Oldershaw trays. The bottoms from the stripper column contained the reaction product. The stripper overhead contained the ammonia.

The bottoms from the stripper column was fed to the base of a distillation column configured analogously to the stripper column. The column head pressure was maintained at 50 torr, and the bottoms temperature was 204 degrees C. A mixture of 84% ACN and 15% HMD was removed as a side draw between the BX packing and the Oldershaw sections. The bottoms was 93.5% ADN with 4.5% ACN and about 0.65% high boilers. The distillate contained 98% HMD, 1150 ppm THA, 0.15% ACN, and 1.15% HMI (area percent analysis of gas chromatogram). This distillate was used in the following hydrogenation reactions.

The distillate was analyzed by gas chromatography using a calibrated method, and was shown to contain 0.73% HMI (different analytical method from that described above) and 1300 ppm THA. This distillate (50 g) was charged to a 100 cc pressure vessel with 2 g of Raney® Ni 2400 slurry (W.R. Grace Co.). The reactor was purged with nitrogen, tested for leaks, and then charged with hydrogen to approximately 621 kPa (90 psig) pressure and heated to 90 degrees C., at which point the pressure was increased to 3447 kPa (500 psig). After 180 minutes, a sample was withdrawn from the reactor and analyzed by gas chromatography. The sample contained 0.86% HMI, 84 ppm THA.

The sample will then be introduced into a standard distillation column operating at atmospheric pressure to remove the HMI as distillate and to remove as bottoms HMD with low THA content.

What is claimed is:

1. A process for co-producing HMD and ACN from ADN, wherein the HMD contains less than 200 ppm THA, said process comprising the steps of:
   (1) contacting ADN and hydrogen in the presence of a hydrogenation catalyst to produce a reaction product that comprises HMD, ACN, THA, and unreacted ADN;
   (2) distilling the reaction product to provide a distillate that comprises HMD and THA;
   (3) contacting the distillate with hydrogen in the presence of a hydrogenation catalyst, thereby providing a hydrogenation product that comprises HMD and HMI, said hydrogenation product containing less than 200 ppm THA; and
   (4) distilling the hydrogenation product to provide a final distillate that comprises HMI and a bottoms that comprises HMD that contains less than 200 ppm THA and is substantially free of HMI.

2. The process of claim 1 wherein the hydrogenation catalyst of step (3) is Raney Nickel or Raney Cobalt.

* * * * *